(12) United States Patent
Mott et al.

(10) Patent No.: US 10,183,008 B2
(45) Date of Patent: Jan. 22, 2019

(54) TREATMENT OF PROLONGED STATUS EPILEPTICUS

(71) Applicant: University of South Carolina, Columbia, SC (US)

(72) Inventors: David D. Mott, Columbia, SC (US); Janet L. Fisher, Columbia, SC (US); Rene H. Levy, Seattle, WA (US); Marie-Emmanuelle LeGuern, Compiegne (FR); Marc Verleye, Compiegne (FR); Bernard Hublot, Compiegne (FR)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 13/622,596

(22) Filed: Sep. 19, 2012

(65) Prior Publication Data

US 2013/0079336 A1    Mar. 28, 2013

Related U.S. Application Data

(63) Continuation of application No. 13/367,746, filed on Feb. 7, 2012, now abandoned.
(Continued)

(51) Int. Cl.
| | |
|---|---|
| *A61K 31/357* | (2006.01) |
| *A61K 31/5513* | (2006.01) |
| *A61K 31/135* | (2006.01) |
| *A61K 31/165* | (2006.01) |
| *A61K 31/167* | (2006.01) |
| *A61K 31/20* | (2006.01) |
| *A61K 31/36* | (2006.01) |

(Continued)

(52) U.S. Cl.
CPC ......... *A61K 31/357* (2013.01); *A61K 31/135* (2013.01); *A61K 31/165* (2013.01); *A61K 31/167* (2013.01); *A61K 31/20* (2013.01); *A61K 31/36* (2013.01); *A61K 31/4015* (2013.01); *A61K 31/4166* (2013.01); *A61K 31/515* (2013.01); *A61K 31/55* (2013.01); *A61K 31/5513* (2013.01); *A61K 31/5517* (2013.01); *A61K 31/661* (2013.01); *A61K 31/7048* (2013.01)

(58) Field of Classification Search
None
See application file for complete search history.

(56) References Cited

U.S. PATENT DOCUMENTS 3,910,959 A    10/1975    Vallet
5,095,033 A *    3/1992    Levy et al. ............ 514/464

OTHER PUBLICATIONS

W. Allen Hauser. Status epilepticus: epidemiological considerations. Neurology, 40, Suppl. 2, May 1990.*
(Continued)

*Primary Examiner* — Anna Pagonakis
(74) *Attorney, Agent, or Firm* — Dority & Manning, P.A.

(57) ABSTRACT

Methods for terminating, preventing, and/or treating status epilepticus are generally provided. The method can include administering a prophylactically or therapeutically effective amount of stiripentol or a related compound thereof to an individual in need of treatment of status epilepticus. The individual can be in need of treatment of prolonged status epilepticus, refractory status epilepticus, and/or benzodiazepine-resistant status epilepticus.

10 Claims, 9 Drawing Sheets

STP is a weakly selective positive allosteric modulator of the GABA$_A$ receptor

A.

B.

STP (100µM) increases GABA (0.3µM) current at all tested GABA$_A$R subunit combinations (n=5-9). (Fisher JL, *Neuropharmacol.* 56:190-197, 2009)

Related U.S. Application Data

(60) Provisional application No. 61/462,908, filed on Feb. 9, 2011, provisional application No. 61/463,814, filed on Feb. 23, 2011.

(51) Int. Cl.
| | | |
|---|---|---|
| *A61K 31/4015* | (2006.01) | |
| *A61K 31/4166* | (2006.01) | |
| *A61K 31/515* | (2006.01) | |
| *A61K 31/55* | (2006.01) | |
| *A61K 31/5517* | (2006.01) | |
| *A61K 31/661* | (2006.01) | |
| *A61K 31/7048* | (2006.01) | |

(56) References Cited

OTHER PUBLICATIONS

Chiron et al. Stiripentol in childhood partial epilepsy: randomized placebo-controlled trial with enrichment and withdrawal design. J. Child Neurol. 2006; 21: 496-502.*

Thanh et al., "Long term efficacy and tolerance of stiripentol in severe myoclonic epilepsy of infancy (Dravet's syndrome)" Archives de Pédiatrie 9 (2002) p. 1120-1127.

Inoue at al., "Stiripentol open study in Japanese patients with Dravet syndrome" Epilepsia, 50 (11) (2009), p. 2362-2368.

* cited by examiner

A. STP (100μM) potentiates the IPSC in the presence of clobazam (CLB, 10μM, n=4)

B. Potentiation by CLB (10μM) and DZP (1μM), but not STP (100μM), is blocked by flumazenil (FMZ, 10μM), a BZD-site antagonist (n=4)

A. DZP (300nM), but not STP (100 µM), is significantly less effective at potentiating the IPSC during prolonged SE (n=4-9)

B. DZP (1µM), but not STP (100 µM), is less effective at potentiating tonic current during prolonged SE (n=3-4)

TREATMENT OF PROLONGED STATUS EPILEPTICUS

PRIORITY INFORMATION

The present application claims priority to and is a continuation of U.S. patent application Ser. No. 13/367,746 filed on Feb. 7, 2012 titled "Treatment of Prolonged Status Epilepticus" of Mott, et al., which claims priority to U.S. Provisional Patent Application Ser. No. 61/462,908 filed on Feb. 9, 2011 titled "Treatment of Prolonged Status Epilepticus" of Mott, et al. and U.S. Provisional Patent Application Ser. No. 61/463,814 filed on Feb. 23, 2011 titled "Treatment of Prolonged Status Epilepticus" of Mott, et al.; all of which are incorporated by reference herein.

BACKGROUND OF INVENTION

Status epilepticus (SE) is a life-threatening condition in which the brain is in a continuous state of seizure. Rapid seizure control is essential to reduce morbidity and mortality. Benzodiazepines (BZDs), such as diazepam (DZP), which enhance $GABA_A$ receptor-mediated inhibition, are the first-line therapy for the treatment of SE. Despite their effectiveness, at least 35% of patients with generalized convulsive SE are refractory to BZDs. In addition, evidence from clinical and animal studies indicates that successful treatment of SE with BZDs is negatively affected by seizure duration. Pharmacoresistance to BZDs develops rapidly after the initiation of SE. Indeed, rodent studies have shown an approximate 9-10 fold decrease in the efficacy of diazepam at terminating prolonged SE (45 minutes after onset). The development of pharmacoresistance during SE is due in part to a selective decrease in benzodiazepine-sensitive populations of $GABA_A$ receptors, leaving a population of receptors that is not modulated by these drugs. Specifically, BZDs only act at $GABA_A$ receptors containing γ subunits and SE decreases surface expression of $GABA_A$ receptors containing γ2 subunits.

As such, a need exists for an improved method of treating and/or preventing SE that minimizes the development of pharmacoresistance during treatment.

SUMMARY OF THE INVENTION

Objects and advantages of the invention will be set forth in part in the following description, or may be obvious from the description, or may be learned through practice of the invention.

Methods are generally provided for terminating, preventing, and/or treating status epilepticus. For example, the method can include administering a prophylactically or therapeutically effective amount of stiripentol or a related compound thereof to an individual in need of treatment of status epilepticus. In certain embodiments, the individual is in need of treatment of prolonged status epilepticus, refractory status epilepticus, and/or benzodiazepine-resistant status epilepticus.

In one particular embodiment, the stiripentol or a related compound thereof has the formula:

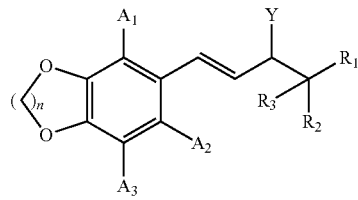

in which: n represents 1 or 2; $A_1$ represents a hydrogen atom, a halogen atom, or a linear or branched alkyl group having from 1 to 4 carbon atoms; $A_2$ represents a hydrogen atom, a halogen atom, or a linear or branched alkyl group having from 1 to 4 carbon atoms; $A_3$ represents a hydrogen atom, a halogen atom, or a linear or branched alkyl group having from 1 to 4 carbon atoms; $R_1$ represents a hydrogen atom or a linear or branched alkyl group having from 1 to 4 carbon atoms; $R_2$ represents a hydrogen atom or a linear or branched alkyl group having from 1 to 4 carbon atoms; $R_3$ represents a hydrogen atom or a linear or branched alkyl group having from 1 to 4 carbon atoms; and V represents —OH, =O or —SH. For example, in particular embodiments, Y can be —OH; $R_1$, $R_2$, and $R_3$ can be identical; $A_1$, $A_2$, and $A_3$ can be identical (e.g., each of $A_1$, $A_2$, and $A_3$ can represent a hydrogen atom); and/or n can be 1.

For example, the stiripentol or a related compound thereof can have the formula:

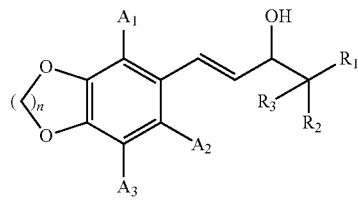

in which: n represents 1 or 2; $A_1$ represents a hydrogen atom, a halogen atom, or a linear or branched alkyl group having from 1 to 4 carbon atoms; $A_2$ represents a hydrogen atom, a halogen atom, or a linear or branched alkyl group having from 1 to 4 carbon atoms; $A_3$ represents a hydrogen atom, a halogen atom, or a linear or branched alkyl group having from 1 to 4 carbon atoms; and $R_1$ represents a hydrogen atom or a linear or branched alkyl group having from 1 to 4 carbon atoms.

The stiripentol or a related compound thereof can be, in certain embodiments, combined with at least one additional compound intended for preventing or treating status epilepticus, in particular prolonged status epilepticus, refractory status epilepticus, or benzodiazepines-resistant status epilepticus. For instance, the at least one additional compound can be selected from the group constituted of a benzodiazepine; phenytoin; fosphenytoin; carbamazepine; valproate; levetiracetam; topiramate; lacosamide; barbiturates; general anesthetics; lidocaine; ketamine; and combinations thereof. In one embodiment, the additional compound can include a benzodiazepine (e.g., diazepam, clonazepam, lorazepam, midazolam, or a combination thereof).

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

DEFINITIONS

Figure 1:
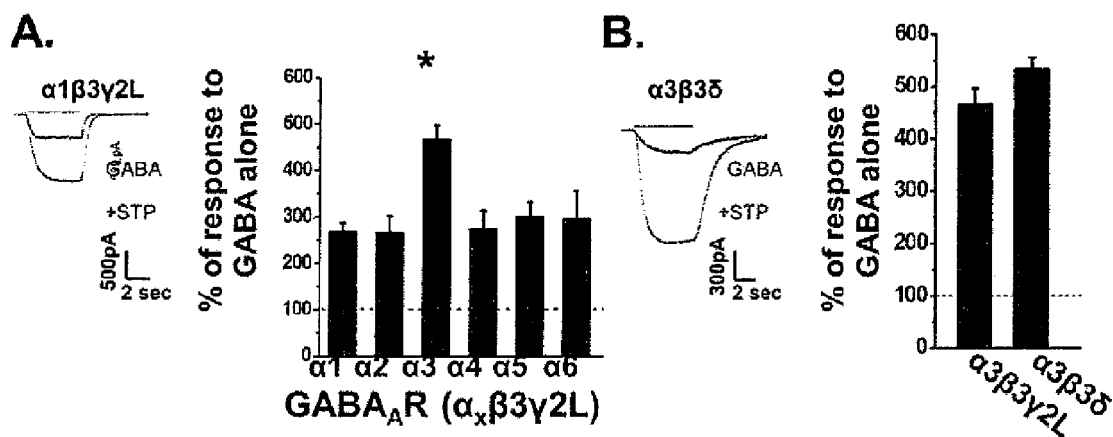
FIG. 1 shows that STP (100 μM) increases GABA (0.3 μM) current at all tested $GABA_AR$ subunit combinations (n=5-9) (from Fisher J L, Neuropharmacol. 56:190-197, 2009). Methods: Full-length cDNAs for rat $GAB_AR$ α1, α3-6, β3, γ2, δ and human α2 subunits were transfected into the HEK-293T cell line using calcium phosphate precipitation. For selection of transfected cells, 1 μg of the plasmid pHook™-1 (Invitrogen) containing cDNA encoding the surface antibody sFv was also transfected into the cells. The selected cells were resuspended into DMEM, plated onto glass coverslips treated with poly L-lysine and coated with collagen and used for recordings 18-28 hrs later. Whole-cell recordings were performed with an external solution containing (in mM): 142 NaCl, 8.1 KCl, 6 $MgCl_2$, 1 $CaCl_2$, and 10 HEPES (pH 7.4, 295-305 mOsm). Recording electrodes were filled with an internal solution consisting of (in mM): 153 KCl, 1 $MgCl_2$, 5 K-EGTA and 10 HEPES. GABA was applied to cells using a stepper solution exchanger with a complete exchange time of <50 msec (open tip).
Figure 2:
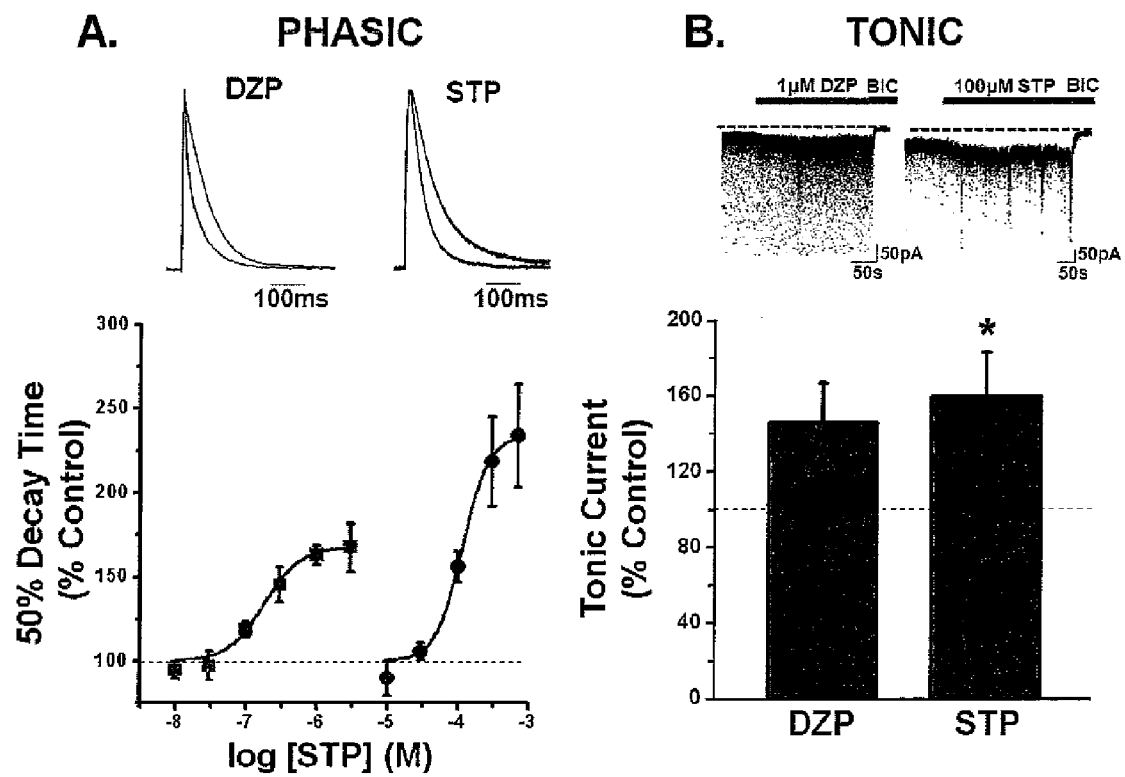
FIG. 2 shows a brain slice electrophysiology that is used to show that DZP and STP potentiate both phasic (panel A) and tonic (panel B) inhibition: A. DZP (1 μM) and STP (100 μM) potentiate $GABA_A$ inhibitory postsynaptic currents (IPSCs) with $EC_{50}$s of 170 nM and 115 μM, respectively (n=2-7), and B. 1 μM DZP and 100 μM STP both increase tonic inhibition.
Figure 3:
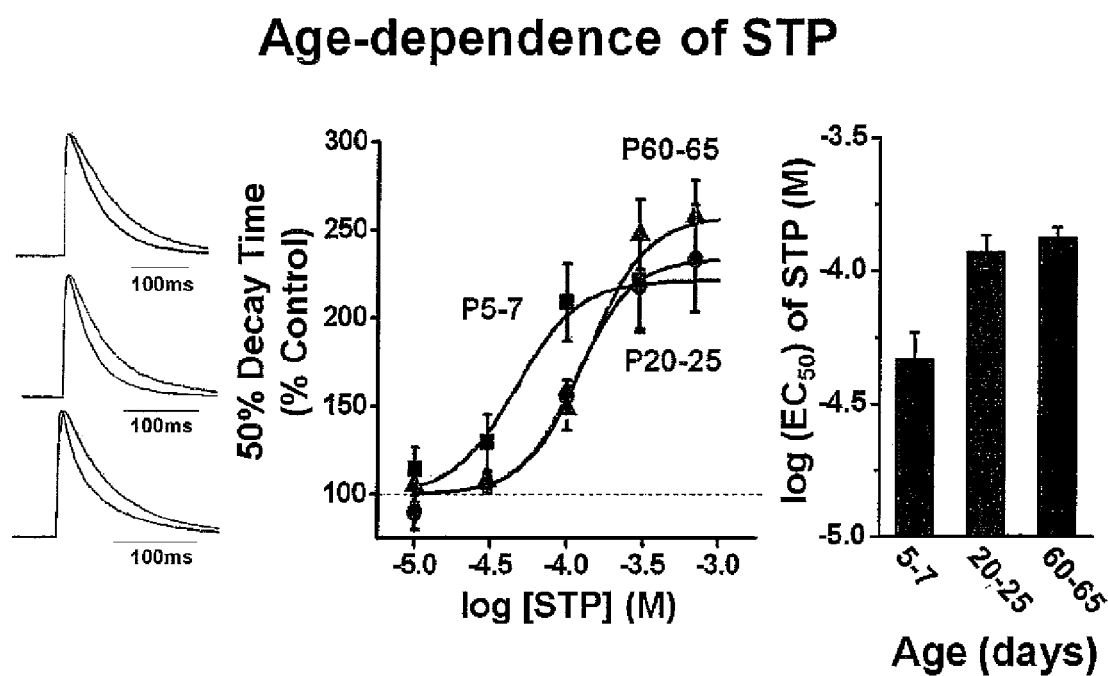
FIG. 3 shows potentiation by STP of the GABAergic IPSC is age-dependent: Potentiation by STP was measured in three distinct age groups, postnatal day 5-8 (n=4-7), postnatal day 20-25 (n=5-9) and postnatal day 60-65 (n=5-9). STP was significantly more effective in potentiation of the evoked IPSC in postnatal day 5-9 animals, as compared to postnatal 60-65 (**p<0.01), indicating an age-dependent potentiation by STP.
Figure 4:
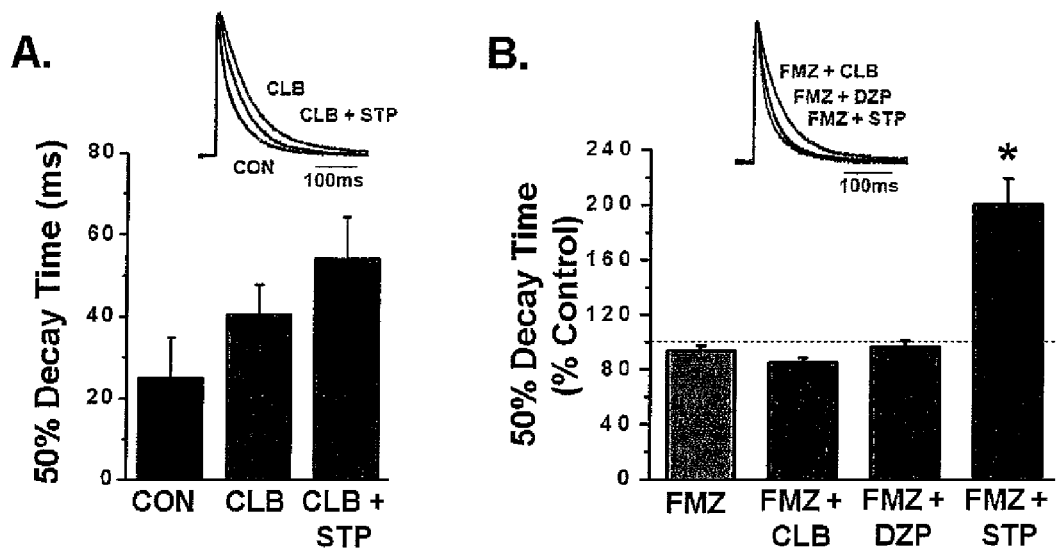
FIG. 4 shows potentiation of GABAergic transmission by STP is independent of the benzodiazepine (BZD)-binding site: A. STP (100 μM) potentiates the $GABA_A$ IPSC in the presence of the BZD agonist, clobazam (CLB, 10 μM, n=4), and B. Potentiation by CLB (10 μM) and DZP (1 μM), but not STP (100 μM), is blocked by flumazenil (FMZ, 10 μM), a BZD-site antagonist (n=4).
Figure 5:
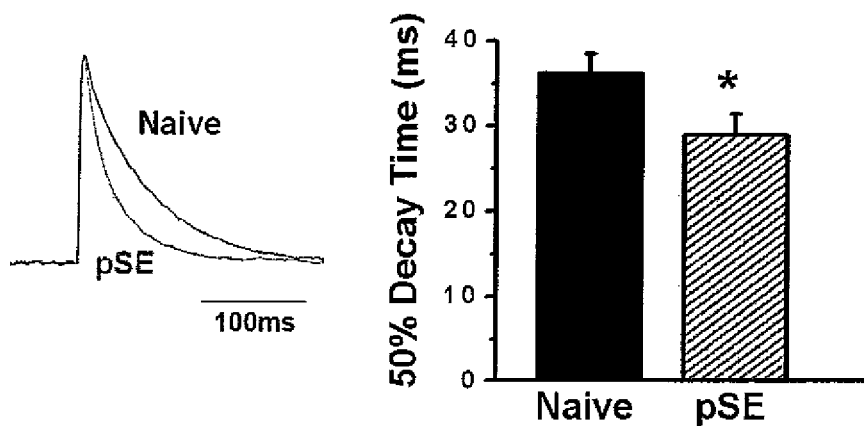
FIG. 5 shows that kinetics of the $GABA_A$ IPSC are significantly (*p<0.05) faster in animals exposed to prolonged SE (45 minutes of continuous seizure activity, n=39), as compared to naïve animals (n=36) (*p<0.05). Alterations in IPSC kinetics were measured by changes in the 50% decay time of the evoked current.
Figure 6:
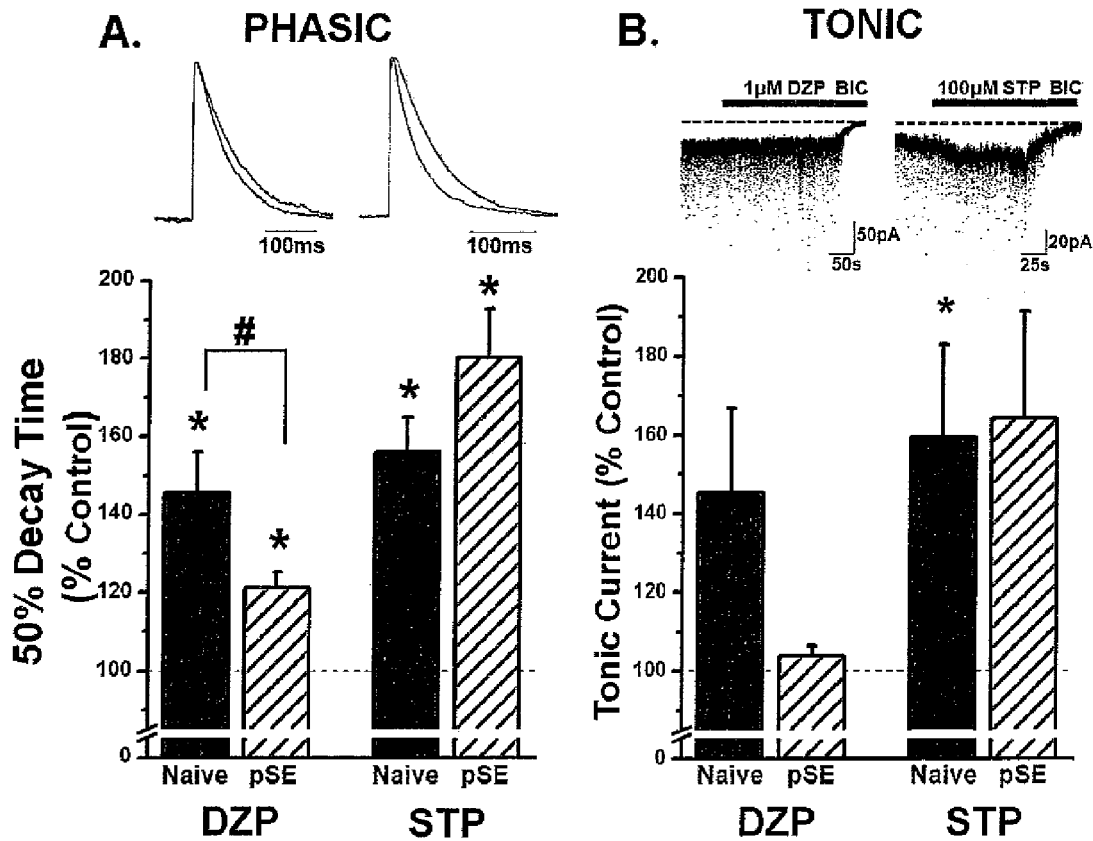
FIG. 6 shows that STP, but not DZP, remains effective in potentiating GABAergic inhibition during prolonged SE: A. DZP (300 nM), but not STP (100 μM), is significantly less effective at potentiating the $GABA_A$ IPSC during prolonged SE (n=4-9), and B. DZP (1 μM), but not STP (100 μM), is less effective at potentiating tonic current during prolonged SE (n=3-4).
Figure 7:
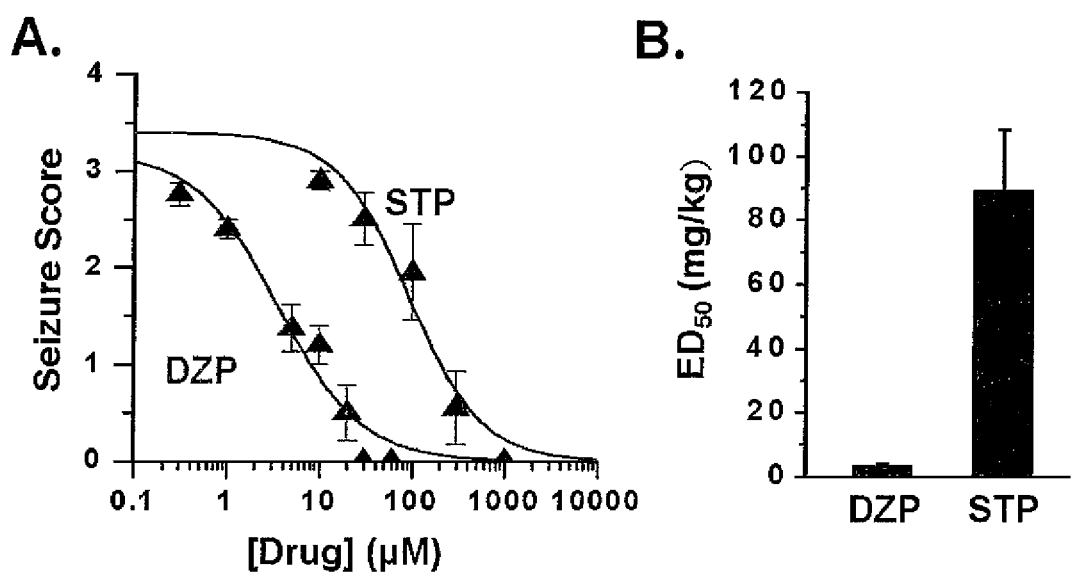
FIG. 7 shows behavioral studies that were used to determine that STP and DZP both terminate brief behavioral convulsions in the lithium-pilocarpine model of S.E. Seizures were induced in postnatal 20-25 day old male rats. DZP (n=4-19) or STP (n=4-10) was administered at the onset of the first stage 3 behavioral convulsion. Based on the Racine scale, seizure scores were taken 15 minutes following administration of DZP or STP and plotted against the dose of the drug administered. The $ED_{50}$ was determined based on the fit of the sigmoidal dose-response curve.
Figure 8:
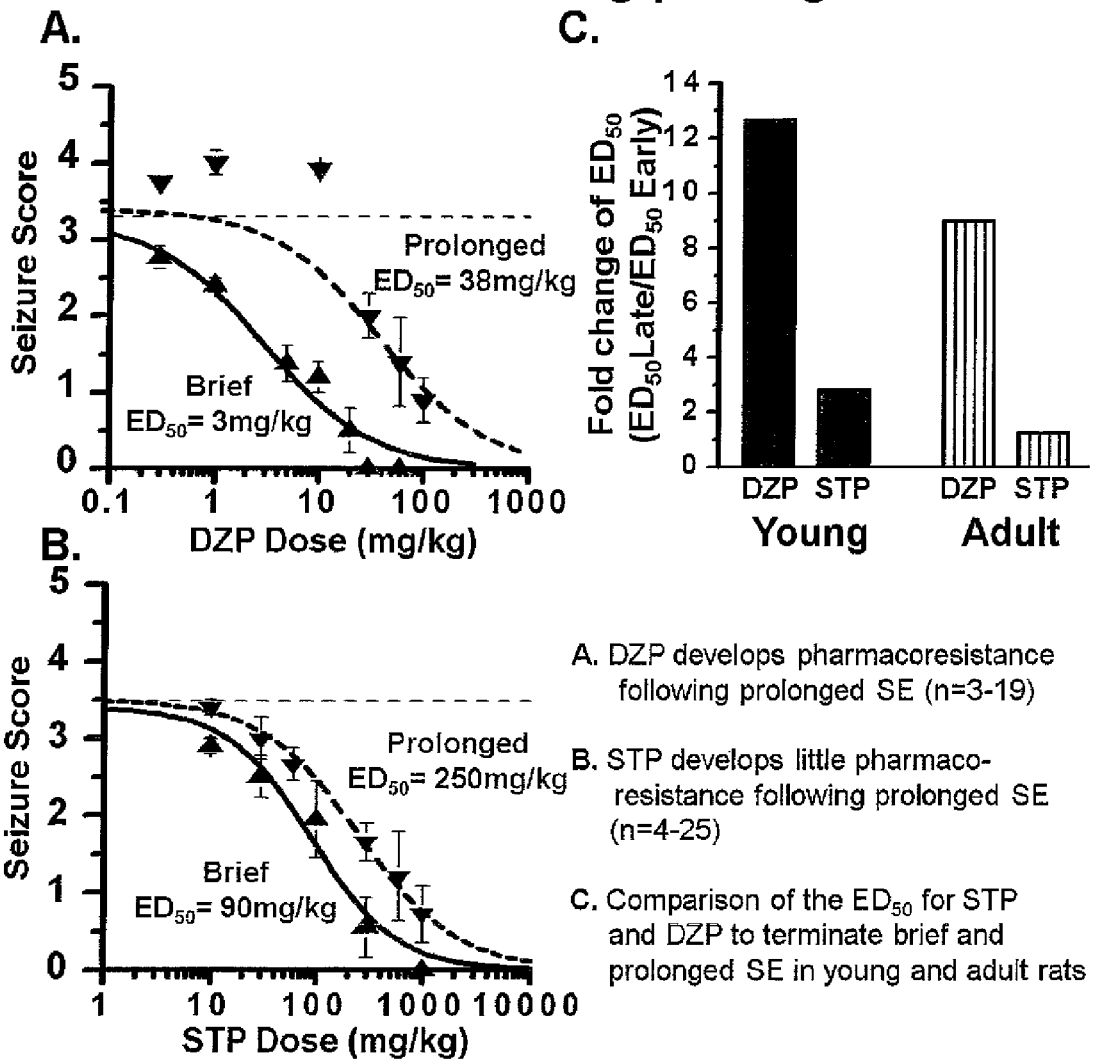
FIG. 8 shows that less pharmacoresistance develops to STP than DZP during prolonged SE: A. DZP develops pharmacoresistance following prolonged SE (n=3-19), indicated by an increase in the DZP $ED_{50}$ for seizure termination, and B. STP develops little pharmacoresistance following prolonged SE (n=4-25). C. Comparison of the $ED_{50}$ for STP and DZP to terminate brief and prolonged SE in young and adult rats. Fold change was calculated by dividing $ED_{50}$ after prolonged SE by $ED_{50}$ after brief SE. The shift in $ED_{50}$ was substantially smaller for STP, indicated reduced pharmacoresistance after prolonged SE.
Figure 9:
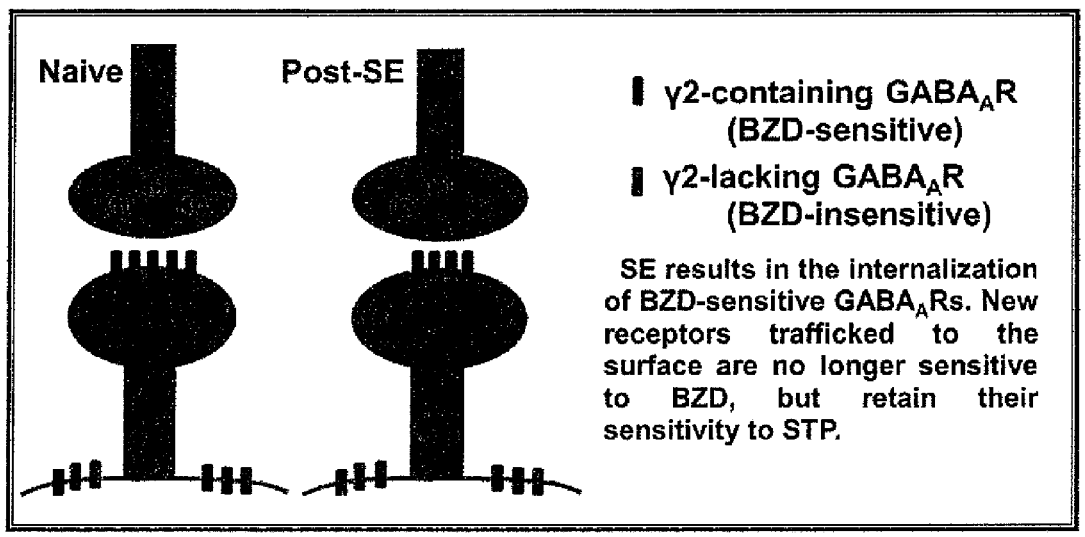
FIG. 9 shows a potential model that SE results in the internalization of BZD-sensitive $GABA_A$ receptors. New $GABA_A$ receptors trafficked to the surface during SE are no longer sensitive to BZD, but retain their sensitivity to STP. According to this model, the subunit selectivity of STP enables it to remain effective in BZD-resistant SE.

As used herein, the term "stiripentol" encompasses both stiripentol and related compounds thereof, unless otherwise specifically stated. Stiripentol (STP), which is also known as a 1-(3,4-methylenedioxyphenyl)-4,4-dimethylpent-1-en-3-ol, belongs to the group of aromatic allylic alcohols. The structure of stiripentol can be represented as follows:

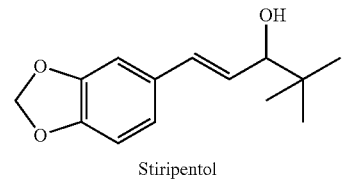 [SMILES: CC(C)(C)C(O)/C=C/c1ccc2c(c1)OCO2]

Stiripentol

As used herein, the term "related compounds thereof" refers to compounds that have the basic structure of stiripentol with substituted atom(s) and/or substituted side groups, while still keeping the functionality of stiripentol.

The term "pharmaceutically effective amount" refers to that amount of a drug or pharmaceutical agent that will elicit the biological or medical response of a tissue, system, animal, or human that is being sought by a researcher or clinician. This amount can be a therapeutically effective amount.

DETAILED DESCRIPTION OF INVENTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Methods are generally disclosed for terminating status epilepticus via administering a prophylactically or therapeutically effective amount of stiripentol or a related compound thereof to a subject. Simply put, it has been surprisingly found that stiripentol effectively terminates status epilepticus and that it remains effective during prolonged status epilepticus, even when the status epilepticus has become resistant to BZDs. Thus, in one particular embodiment, it has been surprisingly found that stiripentol and its analogues can be effective for treating and preventing pharmacoresistant status epilepticus.

Without wishing to be bound to any particular theory, it is believed that stiripentol likely terminates status epilepticus by potentiating GABAergic inhibition. In particular, it has been found that stiripentol potentiates $GABA_A$ receptor-mediated currents to a similar extent in control and during prolonged status epilepticus. In contrast, BZDs lose effectiveness during prolonged status epilepticus. The ability of stiripentol to remain effective during prolonged status epilepticus is likely due to its ability to potentiate $GABA_A$ receptor-mediated currents in a weakly subunit dependent manner. Thus, unlike BZDs, stiripentol remains effective despite changes in $GABA_A$ receptor subunit composition during status epilepticus.

Based on the above discoveries, the use of stiripentol or related compounds thereof for treating and/or preventing status epilepticus (SE), in particular prolonged status epilepticus, refractory status epilepticus and benzodiazepine-resistant (BZD-resistant) status epilepticus. In one particular embodiment, a method for the prevention and/or treatment of status epilepticus, in particular prolonged status epilepticus, refractory status epilepticus or BZD-resistant status epilepticus treatment, in an individual, comprising administering a prophylactically or therapeutically effective amount of stiripentol or related compounds. Additionally, in one embodiment, stiripentol or related compounds thereof can be combined with at least one additional compound intended for preventing or treating status epilepticus, in particular prolonged status epilepticus, refractory status epilepticus or BZD-resistant status epilepticus.

I. Status Epileticus

Status epilepticus (SE) is a life-threatening condition in which the brain is in a continuous state of seizure. As used herein, "status epilepticus" refers to a continuous unremitting seizure lasting longer than 30 minutes, or to recurrent seizures without regaining consciousness between seizures for more than 30 minutes. Prolonged status epilepticus preferably relates to status epilepticus lasting at least 45 minutes. Refractory status epilepticus preferably relates to status epilepticus lasting at least 60 minutes. BZD-resistant status epilepticus preferably relates to status epilepticus which does not end upon administration of a benzodiazepine (BZD), such as diazepam, clonazepam, lorazepam, or midazolam.

Benzodiazepines (BZDs), which enhance $GABA_A$ receptor mediated inhibition, are the first-line therapy for treatment of status epilepticus. However, treatment with BZDs is negatively affected by seizure duration. Pharmacoresistance to BZDs develops rapidly after the initiation of SE. This is due to a selective decrease in BZD-sensitive $GABA_A$ receptors during status epilepticus.

II. Stiripentol and Related Compounds Thereof

Stiripentol is structurally unrelated to any other currently available antiepileptic drug, which acts as a positive allosteric modulator of $GABA_A$ receptors. Unlike DZP, stiripentol potentiates $GABA_A$ receptors in a weakly subunit dependent manner (see, FIG. 1).

In one particular embodiment, stiripentol or related compounds thereof can be represented by the formula (I):

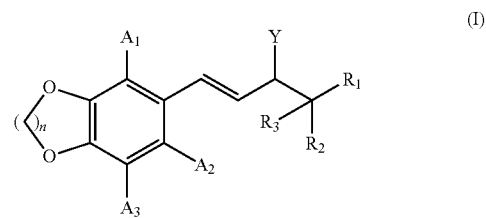

in which: n represents 1 or 2; $A_1$, $A_2$ and $A_3$ are identical or different, and individually represent a hydrogen atom, a halogen atom, or a linear or branched alkyl group having from 1 to 4 carbon atoms; $R_1$, $R_2$ and $R_3$ are identical or different, and individually represent a hydrogen atom or a linear or branched alkyl group having from 1 to 4 carbon atoms; and Y represents —OH, =O or —SH.

Preferred alkyl groups according to the invention encompass the methyl, ethyl, n-propyl, isopropyl, n-butyl, s-butyl and t-butyl groups. The Cl, I, Br or F atoms are preferred halogen atoms according to the invention.

For example, the stiripentol or related compounds thereof can be represented, in a preferred embodiment, by the formula (II):

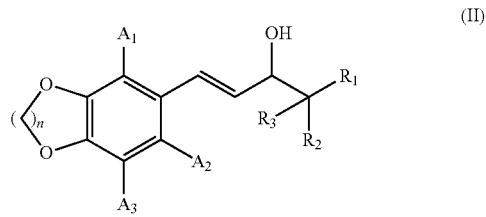

in which: n, $A_1$, $A_2$, $A_3$ and $R_1$ are as defined above with respect to formula (I).

Even more preferably, the above-defined compound of formula (I) or (II) can be represented by the following formula (III):

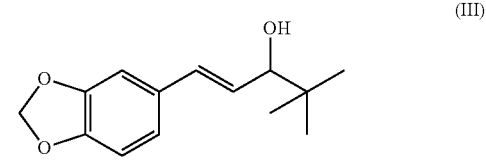 [SMILES: CC(C)(C)C(O)/C=C/c1ccc2c(c1)OCO2]

As will be clear to one of skill in the art, the above-defined formulas (I), (II), and (III) represent either the various stereoisomers encompassed by these formulas or mixtures thereof, in particular racemic mixtures thereof.

Thus, the compound of formula (III) can be a compound of formula (IIIa) a compound of formula (IIIb), or a mixture of a compound of formula (IIIa) and a compound of formula (IIIb), in particular the racemic mixture thereof.

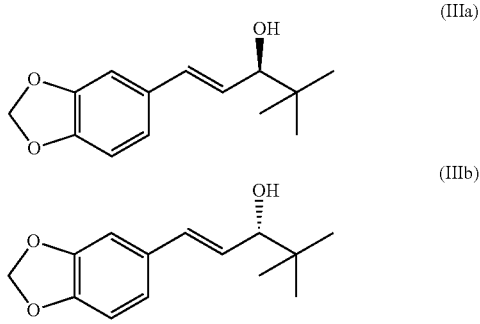

French patent FR 2 173 691, which is incorporated herein by reference, describes the synthesis of stiripentol, in particular starting from methylenedioxy-3,4-phenyl)-1-dimethyl-4,4-penten-1-on-3. It is well within the ordinary skills of one of skill in the art to synthesize the other compounds of formula (I) from this teaching.

In addition, pharmaceutically acceptable salts of stiripentol or related compounds thereof can be used in accordance with the disclosed methods. Besides, in accordance with the invention one or several pharmaceutically acceptable carriers or excipients may be administered with stiripentol or related compounds according to the invention. For example, the compound of formula (I) as defined above or the pharmaceutically acceptable salt thereof, can be administered at a unit dose of from 100 mg to 1000 mg. Preferably, the compound of formula (I) as defined above or the pharmaceutically acceptable salt thereof can be administered with a dosage regimen of from 10 mg/kg/d to 200 mg/kg/d. For instance, the compound of formula (I) as defined above or the pharmaceutically acceptable salt thereof, can be in a form suitable for administration by the oral route. As such, the compound of formula (I) as defined above or the pharmaceutically acceptable salt thereof can be in the form of sachets, tablets or capsules.

As intended herein, the expression "compound intended for preventing or treating for preventing or treating SE, in particular prolonged SE, refractory SE or BZD-resistant SE" relates to any compound intended to alleviate one or more of the symptoms of SE, in particular prolonged SE, refractory SE or BZD-resistant SE. Preferably, the at least one additional compound intended for preventing or treating SE, in particular prolonged SE, refractory SE or BZD-resistant SE as defined above, is selected from the group constituted of a benzodiazepine (BZD), such as diazepam, clonazepam, lorazepam, or midazolam; phenytoin; fosphenytoin; carbamazepine; valproate; levetiracetam; topiramate; lacosamide; barbiturates, such as phenobarbital, thiopental, or pentobarbital; general anesthetics, such as propofol; lidocaine; and ketamine.

As intended herein "combined" means that stiripentol, or related compounds, are administered at the same time than the additional compound, either together, i.e. at the same administration site, or separately, or at different times, provided that the time period during which stiripentol, or related compounds, exert their pharmacological effects on the individual and the time period during which the additional compound exerts its pharmacological effects on the individual, at least partially intersect.

In this regard, the present invention also relates to pharmaceutical composition comprising stiripentol, or related compounds as previously defined, and a least one additional compound intended for preventing or treating SE, in particular prolonged SE, refractory SE or BZD-resistant SE as defined above. The pharmaceutical composition optionally further comprises at least one pharmaceutically acceptable carrier or excipient.

III. Examples of Treating SE with Stiripentol or Related Compounds Thereof

The use of stiripentol as an anticonvulsant in BZD-resistant rats was explored. Additionally, the effect of age in the use of stiripentol as an anticonvulsant in BZD-resistant rats was explored.

Experiments were performed on male rats age 5-65 days. SE was induced using lithium pilocarpine. Brief SE was defined as the onset of stage 3 seizures. Prolonged SE was defined as 45 minutes of SE following the first stage 3 seizure. It was found that pharmacoresistance developed to diazepam (DZP) following prolonged SE (12.5 fold shift in DZP $E_{50}$). Stiripentol was also anticonvulsant in this model and displayed substantially less pharmacoresistance than DZP during prolonged SE (2.7 fold shift in STP $ED_{50}$). The anticonvulsant effect of stiripentol, but not DZP was reduced in 60-65 compared to 20-25 day old rats.

In confirmatory studies, whole-cell brain slice electrophysiology were used to study stiripentol modulation of inhibitory post-synaptic currents (IPSCs) in dentate gyrus granule cells. It was found that, like DZP, stiripentol prolonged IPSC decay in rats aged 5 to 65 days old. However, the extent of stiripentol prolongation was age-dependent with the greatest effect in young rats. During prolonged SE, both DZP and stiripentol became less effective at potentiating IPSCs. However, the decrease in the effect of stiripentol was substantially less than that of DZP.

Without wishing to be bound to a particular theory, it is believed that the activity of stiripentol at α4 and/or δ-containing $GABA_A$ receptors contributes to its reduced pharmacoresistance during prolonged SE, while the higher activity of stiripentol at α3-containing $GABA_A$ receptors accounts for its age-dependent effects.

Drugs targeting α4 and/or δ-containing $GABA_A$ receptors may thus be of benefit in treatment of BZD-resistant SE. Thus, it was found that stiripentol or related compounds thereof may be of therapeutic benefit in the prevention and/or the treatment of status epilepticus, in particular prolonged SE, refractory SE and BZD-resistant SE.

Materials and Methods

Brain Slice Electrophysiology—

Brain slices were prepared from isoflurane-anesthetized rats (5-65 days old) that were either naïve or had experienced prolonged SE. Transverse 300 μm thick slices were cut using a vibratome (Leica VT1000S, Nussloch, Germany). Brain slices were prepared in cold (4° C.), oxygenated (95% O2/5% CO2) sucrose-based 'cutting' artificial cerebrospinal fluid (aCSF) that contained (in mM): 248 sucrose, 2 KCl, 1.25 $NaH_2PO_4$, 26 $NaHCO_3$, 10 glucose, 0.5 $CaCl_2$ and 5 $MgSO_4$ (350 mOsm). Slices were incubated for approximately one hour at room temperature in oxygenated (95% $O_2$/5% $CO_2$) aCSF containing (in mM): 125 NaCl, 2.7 KCl, 1.25 $NaH_2PO_4$, 25 $NaHCO_3$, 10 glucose, 0.5 $CaCl_2$ and 7 $MgSO_4$, 0.02 D-APV and 1 kynurenic acid (pH 7.4; 305-312 mOsm). For whole-cell patch-clamp recording, slices were placed in a submerged chamber that was perfused with warm, oxygenated (30-32° C.; 95% $O_2$/5% $CO_2$) aCSF containing (in mM): 125 NaCl, 2.7 KCl, 1.25 $NaH_2PO_4$, 25 $NaHCO_3$, 10 glucose, 2 $CaCl_2$ and 1 $MgSO_4$ (pH 7.4; 305 mOsm). $GABA_A$ IPSCs were recorded from dentate granule cells (DGCs) located in the infra-pyramidal blade of the dentate gyrus, visually identified with infrared-differential interference contrast optics. IPSCs were evoked by stimulation in stratum moleculare of the dentate gyrus near the recording electrode. Stimuli were 0.1 ms, cathodal, monophasic, rectangular constant current pulses (10-100 μA) delivered through monopolar, platinum-iridium stimulating electrodes (FHC Inc, Bowdoin, Me.). IPSCs were recorded using borosilicate glass electrodes (5-8 MΩ) filled with an internal solution containing (in mM): 130 D-Gluconic Acid, 130 CsOH, 7 CsCl, 10 HEPES, 3 QX-314, 2 MgATP, 0.3 Na$_2$GTP, yielding a chloride reversal potential of −42 mV. mIPSC and tonic recordings were performed using an internal solution containing (in mM): 140 CsCl, 10 HEPES, 3 QX-314, 4 MgATP, 0.3 Na$_2$GTP, yielding a chloride reversal potential of 0 mV. Voltage-clamp recordings were made at a holding potential of −20 mV for IPSCs and −60 mV for tonic and mIPSCs. Input and series resistance was monitored throughout the experiment and recordings in which either changed significantly were discarded.

In all experiments IPSCs were pharmacologically isolated using the glutamate receptor antagonists, D-2-amino-5-phosphopentanoic acid (D-APV, 50 μM), or MK-801 maleate (10 μM) and 6-cyano-7-nitroquinoxaline-2,3-dione disodium salt (CNQX, 50 μM), plus the addition of tetrodotoxin (TTX, 1 μM) for mIPSCs and tonic current. Bicuculline methochloride (20 μM) was added at the end of each experiment to confirm that the recorded IPSC was entirely GABAergic. Drugs were perfused for a minimum of 30 minutes in order to obtain a stable baseline. Diazepam and stiripentol, dissolved in DMSO, were prepared as stock solutions which were then diluted in aCSF on the day of the experiment.

Experiments were recorded using a Multiclamp 700B amplifier (Molecular Devices, Sunnyvale, Calif.). Responses were digitized by a Digidata 1440A A-D board (Molecular Devices, Sunnyvale, Calif.) and analyzed using pClamp 10 software. Potentiation of IPSCs was determined by measuring the 20-80% decay segment, while mIPSCs were identified and analyzed by MiniAnalysis software (Synaptosoft, Decatur, Ga.).

Induction of Status Epilepticus (SE) and Seizure Monitoring—

Status epilepticus was induced in male Sprague Dawley rats (5-65 days old; Harlan Sprague Dawley, Indianapolis, Ind.) by intraperitoneal injection of lithium chloride (LiCl) at 127 mg/kg followed 15-20 hr later by scopolamine methylbromide (2 mg/kg) and then pilocarpine at 60 mg/kg. After pilocarpine injection, the rats were observed continuously for occurrence of behavioral seizures. Seizures were scored according to the Racine scale with slight modifications: 0-normal behavior; 1-immobile, staring, curled-up posture; 2-automatisms: repetitive blinking, chewing, head-bobbing, vibrissae twitching, scratching, face-washing; 3-forelimb/hindlimb myoclonic jerking, head tremor; 4-rearing, whole body clonus; 5-loss of posture, rearing and falling. EEG recordings, have established that the cortical electrographic onset of SE corresponds to the onset of forelimb clonus, or stage 3 seizures. Therefore, diazepam or stiripentol was administered either at the onset of S3 seizures (brief SE) or 45 min after S3 seizure onset (prolonged SE). The seizure scores were taken continuously, but specifically 15 mins after the first S3 seizure, and 15 mins after treatment. The scores represented in the data were recorded 15 minutes following treatment. Solutions of lithium, scopolamine, pilocarpine and stiripentol were made fresh on the day of the experiments. Lithium, scopolamine and pilocarpine were dissolved in 0.9% saline. Stiripentol was dissolved in 20% propylene glycol and 80% ethanol. Diazepam was purchased commercially in a solution of 10% propylene glycol and 80% ethanol. All drugs were administered via intraperitoneal (i.p) injection.

The results from these studies are shown in the attached Figures, as discussed above in the Brief Description of the Drawings.

SUMMARY AND CONCLUSIONS

1. DZP and STP were found to prolong GABA mediated synaptic currents in a concentration-dependent manner. Both drugs potentiate tonic current.
2. STP does not act through the benzodiazepine-binding site on the GABA$_A$ receptor.
3. IPSC kinetics were significantly faster following prolonged SE.
4. During prolonged SE, DZP, but not STP, becomes substantially less effective at potentiating both phasic and tonic GABAergic currents.
5. DZP and STP are effective in terminating brief SE
6. Significantly less pharmacoresistance develops to STP, than to DZP, following prolonged SE in both young and adult rats.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method of treating benzodiazepine-resistant status epilepticus, the method comprising:
   administering a therapeutically effective amount of stiripentol to an individual in need of treatment of benzodiazepine-resistant status epilepticus.
2. The method as in claim 1, wherein the individual is in need of treatment of prolonged benzodiazepine-resistant status epilepticus.
3. The method as in claim 1, wherein the individual is in need of treatment of refractory benzodiazepine-resistant status epilepticus.
4. The method as in claim 1, wherein the stiripentol has the formula:

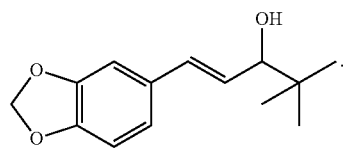 [SMILES: CC(C)(C)C(O)/C=C/c1ccc2c(c1)OCO2]

5. The method as in claim 1, wherein the stiripentol has the formula:

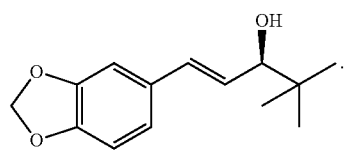 [SMILES: CC(C)(C)[C@H](O)/C=C/c1ccc2c(c1)OCO2]

6. The method as in claim 1, wherein the stiripentol has the formula:

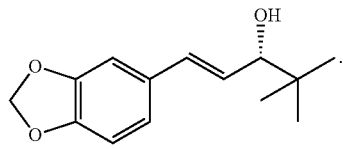

7. The method as in claim 1, wherein the stiripentol is combined with at least one additional compound intended for preventing or treating status epilepticus.

8. The method as in claim 7, wherein the at least one additional compound is selected from the group constituted of a benzodiazepine; phenytoin; fosphenytoin; carbamazepine; valproate; levetiracetam; topiramate; lacosamide; barbiturates; general anesthetics; lidocaine; ketamine; and combinations thereof.

9. The method as in claim 7, wherein the additional compound comprises a benzodiazepine.

10. The method as in claim 9, wherein the benzodiazepine comprises diazepam, clonazepam, lorazepam, midazolam, or a combination thereof.

* * * * *